United States Patent [19]

Cleveland

[11] 4,427,415

[45] Jan. 24, 1984

[54] MANIFOLD VACUUM BIOCHEMICAL TEST METHOD AND DEVICE

[76] Inventor: Patrick H. Cleveland, 4657 Huggins, San Diego, Calif. 92122

[21] Appl. No.: 229,502

[22] Filed: Jan. 29, 1981

Related U.S. Application Data

[63] Continuation of Ser. No. 1,019, Jan. 5, 1979, abandoned.

[51] Int. Cl.³ ............... B01D 25/04; B01D 37/00; G01N 33/56
[52] U.S. Cl. .................. 436/57; 210/232; 210/455; 210/456; 210/767; 422/101; 436/177
[58] Field of Search ............ 422/101; 23/230 B, 920, 23/230.3, 230.6; 210/456, 767, 232, 455, 416.1, 406, 230

[56] References Cited

U.S. PATENT DOCUMENTS

| | | | |
|---|---|---|---|
| 1,762,738 | 6/1930 | Petrey | 422/101 |
| 3,319,792 | 5/1967 | Leder et al. | 422/101 X |
| 3,561,600 | 2/1971 | Kurita et al. | 210/230 X |
| 3,615,257 | 10/1971 | Frost et al. | 422/101 |
| 3,731,806 | 5/1973 | McCormick | 210/406 X |
| 3,888,770 | 6/1975 | Avital et al. | 422/101 X |
| 3,923,463 | 12/1975 | Bagshawe et al. | 422/66 |
| 4,031,197 | 6/1977 | Marinkovich | 23/230 B X |
| 4,090,850 | 5/1978 | Chen et al. | 23/230 B X |
| 4,167,875 | 9/1979 | Meakin | 422/101 X |

*Primary Examiner*—Arnold Turk
*Attorney, Agent, or Firm*—Merchant, Gould, Smith, Edell, Welter & Schmidt

[57] ABSTRACT

A device and method for simultaneous multiple analysis of biochemical substances is described. A manifold plate containing numerous small wells for receiving fluid test media contains a small hole in the bottom of each well; the plate is mounted on a vacuum chamber base which draws the fluid through each well hole leaving suspended solids entrapped on pieces of filter paper inserted in each well. The entrapped substances can then undergo active combination with a series of other reagents added to the wells and again removed via an applied vacuum. After reactions are complete the filter paper and entrapped solids are removed for further analysis.

8 Claims, 8 Drawing Figures

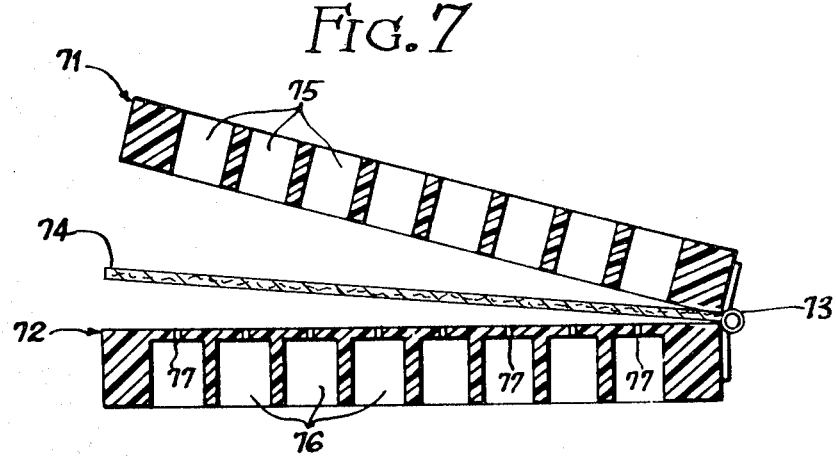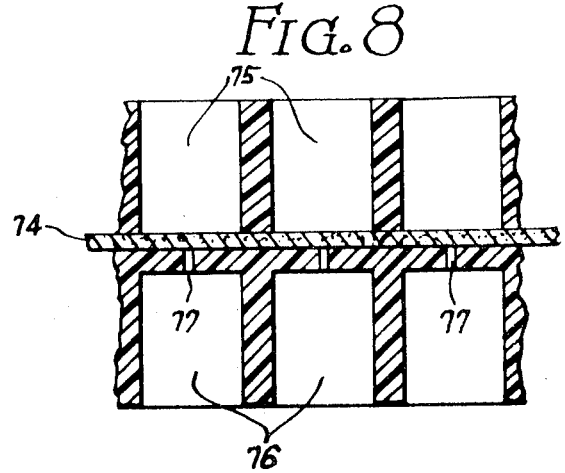

MANIFOLD VACUUM BIOCHEMICAL TEST METHOD AND DEVICE

This is a continuation of application Ser. No. 1,019, filed Jan. 5, 1979, now abandoned.

BACKGROUND OF INVENTION

Traditional methods of laboratory testing of biochemical substances are time-consuming and therefore costly, due to typically repetitive steps required, large numbers of samples that must be tested and retested and the amount and complexity of required laboratory equipment to accomplish the test steps. Many such tests require the sample comprised of particulate or cellular matter suspended in a test medium fluid or in a bodily fluid to undergo active combination with reagents and with intermediate steps of extraction of solid matter and washing with cleansing fluids. The end product of such processes is a residue of solid matter which may be extracted for further analysis by microscopy, reaction in another vessel, radio isotope detection, or spectrophotometery.

Separation of solids from fluid medium may be accomplished by centrifugation, in which a vessel containing the test sample is placed in a mechanical centrifuge and spun until the heavier substances separate to the bottom of the vessel, or simple filtration in which the test fluid is passed through a filtering medium depositing suspended solids which are larger than the filter mesh on the filter, or by gravity separation or absorption in a still laboratory vessel. Filtration methods have the advantage over centrifugation or gravity separation in that they are faster and that several insertions of fluid may be made in the same container and passed through the filter medium, sequentially treating and cleansing the solid material trapped on the filter. In centrifugation or gravity separation the separated fluid must be manually withdrawn from the container before the separated solid may be further washed or treated. Substantial savings of time may be realized therefore by avoiding mechanical removal of fluid from the test container, and in some cases, avoiding removal of the solid material itself to another clean container for further steps. In addition the time required to centrifuge the sample is substantial. The filtration process itself can also be slow however, and may be aided by applying a vacuum to the downstream side of the filter such that the atmospheric pressure differential will force the fluid quickly through the filter. This method can still be time-consuming however, due to limitations of available laboratory equipment and the need for connecting and disconnecting from the laboratory vacuum source the numerous individual containers for samples undergoing tests. Further existing filter manifolds are constructed with exhaust ports whose size permits the fluid to slowly pass through with gravity flow and the fluid will not remain in the container for the length of time necessary to accomplish specific reactions. A separate chamber in such a case would have to be used to accomplish a reaction and transfer to the filter manifold.

Most analytical or quantitative tests of particulate biochemical substances are performed in test tubes or in commercially available containers which provide an array of separate cups drawn together in a grid pattern, usually cast of a plastic, glass or fiberglass solid, enabling simultaneous test of a number of samples. Since the containers are closed wells however, the test steps are subject to the limitations of centrifugation, chemical absorption, or gravity separation and fluids must be drawn off between each test procedure. Efforts to speed this process have involved quite complicated motorized devices to insert and extract fluids from the test wells by passing an array of nozzles over the test wells for inserting fluids and an array of suction ports over the top of the wells to extract fluids.

Finally, all of the methods described above suffer from the dangers of error or contamination of the test samples involved in time-consuming multiple steps, mechanical removal of fluids from the test containers, transfer of the test solids from one container to another, and insertion of instruments such as suction nozzles into the test container.

The device and methology presented herein was developed to facilitate immunodiagnostic tests which were previously difficult to perform. For example, patients with suspected herpes virus infections of the eye usually yield only a few infected cells which can be used to determine the presence or absence of the viral antigens. Because of the numerous manipulations, washing and reaction steps required for immunodiagnostic tests, the cells are often lost in the centrifugation procedures required by these tests. The present invention has been used in conjunction with an indirect radioimmunoassay to detect herpes simplex virus antigens on as few as 195 herpes simplex virus infected human cells. This invention and the accompanying methodology may also be used with direct radioimmunoassays competitive inhibition radioimmunoassays, immunoassays employing fluorescently labeled antibodies, other binding agents (such as staphylococcus aureus protein A) or antigens, or immunoassays employing enzyme labeled antibodies, or other antigens.

Thus it is an object of the present invention to provide a filtration device for chemical and biochemical tests in which a large number of samples may be tested simultaneously.

Another object of the invention is to provide a multiple container test device in which several sequential test steps may be accomplished without removal of the object substance from the test container between test operations.

Another object of the invention is to provide a test method in which large numbers of test samples may be processed without delays for intermediate steps of removal of fluids, transfer of sample containers or mechanical separation.

Another object of the invention is to provide a test method that will separate free reagents from bound reagents rapidly and simultaneously in all samples.

A further object of the invention is to provide an integral vessel for various test steps of different characters, such as filtration and subsequent incubation of samples in the same container to minimize handling of samples in such steps.

Another object of the invention is to provide small reaction chambers in order that only small volumes on the order of 50 microliters of precious reagents need be used.

A final object of the within invention is to provide a simple, inexpensive device which will replace cumbersome, complicated and costly laboratory equipment currently required to perform the tests described above involving numerous sequential test procedures.

SUMMARY OF THE INVENTION

The present invention embodies a cast plate containing an array of small wells for containment of a chemical sample, such as are presently commercially available. The feature unique to the within invention however, is that each well, rather than being a closed receptacle, contains a small hole in its bottom surface through which the fluid sample may pass, the size of the hole being on the order of one millimeter. The entire plate is placed over a second cast element which contains a vacuum chamber large enough to cover the entire lower surface of the manifold arrangement of test wells in the upper plate. A gasket is provided to seal the joint between the upper and lower elements and a vacuum line connection is provided through the lower element in order to apply reduced pressure in the vacuum chamber. A filter medium may be disposed between the test sample containers and the vacuum source eitner by inserting a small disc of filter paper into each test well or by inserting a single sheet of filter paper in a slightly different embodiment of the device adapted to hold the sheet over the drain hole of each test well as described below. Thus a vacuum applied to the vacuum chamber will reduce the pressure at each test well drain hole and rapidly draw the fluid medium through the filter paper, making the deposited solids immediately available for further test procedures.

DESCRIPTION OF THE PRIOR ART

Other commonly known laboratory devices have accomplished some of the objects of the within invention, but applicant claims the combination and unique function as his distinct invention. As discussed before, multiple array test vessels are commercially available, but use either centrigugation or absorption methods of immobilizing reagents, and have not been adapted to apply a suction filtration technique.

Marinkovich, U.S. Pat. No. 4,031,197, describes the test method involving sequential procedures and multiple sample containers in a single test unit, but the method described requires cumbersome physical removal of fluids such as sera and aqueous wash liquids between the procedural steps, resulting in deposit of test solids on a cellulose filter. The within-described suction-filtration technique combined with the multiple sample holder is a marked improvement in the field which enables the sequential steps to be performed more easily, with a larger number of variables and without the lengthy absorption procedure.

Contived methodologies for accomplishment of specific types of tests and limited to the tests for which they are designed also populate the field. An example is Ruhenstroth-Bauer, et al, U.S. Pat. No. 4,018,662, in which a gel carrier for several different reagents is painted on a glass impressed with grooves enabling the plasma to be tested to flow from one groove to the next and sequentially react in each. The within device, however, may be adapted for many different common and complex biochemical analysis sequences without being limited to a specific procedure as Ruhenstroth-Bauer. Other attempts to develop a manifold filtration method have not been adaptable to varying uses or to in-vessel liquid reactions as the small well with pin-hole feature here disclosed makes possible.

BRIEF DESCRIPTION OF THE DRAWINGS

FIG. 7 is a perspective view of an alternate embodiment of the manifold plate.

FIG. 8 is a partial vertical cross section of the manifold plate illustrated in FIG. 7.

DETAILED DESCRIPTION OF THE PREFERRED EMBODIMENT

Figure 1:
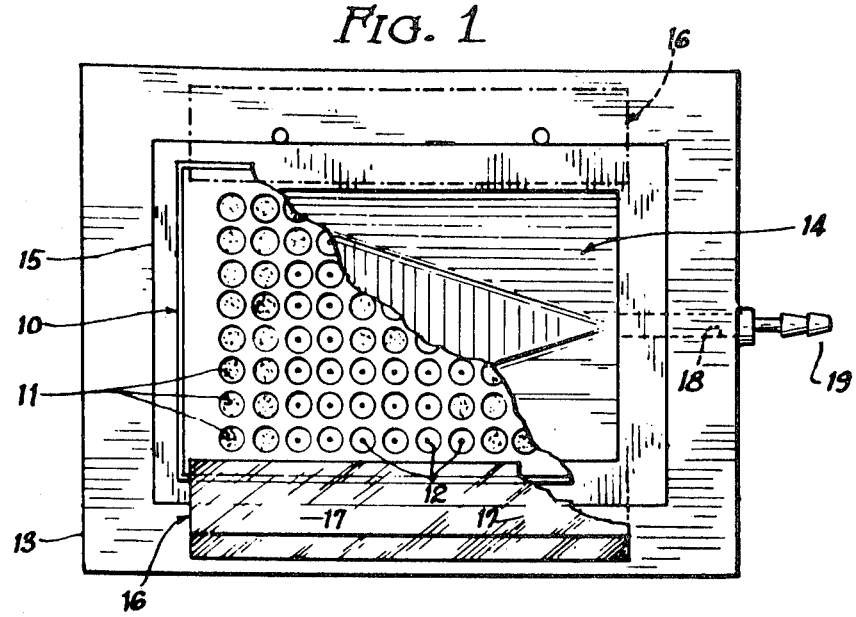
FIG. 1 is a plan view of the assembled device including a cutaway of the top plate to expose the vacuum chamber below.

Referring to the drawings, FIG. 1 illustrates a top view of the assembled device. The primary element of the device is the manifold plate (10) containing a grid array of fluid sample containers (11), the bottom surface of each such sample well containing a drain hole (12). The entire manifold plate is placed over a cast base (13) and the array of sample containers are disposed over a vacuum chamber (14) which is disclosed by the cutaway of the upper right portion of the manifold plate. The bottom surface of the vacuum chamber as shown is formed by three sloping surfaces, the lowest point of each intersecting at the inner end of the vacuum line (18) in order that fluids drawn through the drain holes will collect at the vacuum line and be withdrawn. The joint between the upper manifold plate and the lower cast base is sealed by a rubber gasket (15) and the seal is maintained by pressure applied to the upper plate by the retaining brackets (16) which is in turn held in place by retaining bolts (17). The vacuum line (18) is cast into the base as shown in hidden view and provides a passage from the vacuum chamber to the exterior of the base where it joins with the vacuum nipple (19) which may in turn be connected to a standard laboratory vacuum source via a rubber hose.

Figure 2:
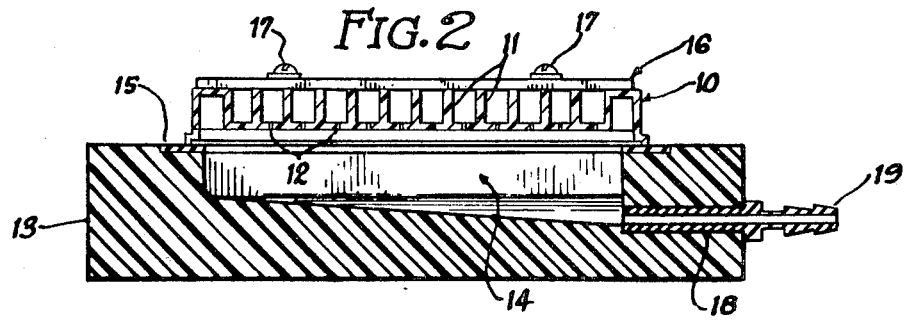
FIG. 2 is a vertical cross section of the device taken across a line coincident with the vacuum fitting of FIG. 1.

The vertical cross section of FIG. 2 more clearly discloses one longitudinal row of sample cups (11) and illustrates that the drain hole (12) in the bottom of each cup is disposed over the vacuum chamber (14). The gasket (15) surrounds the outer perimeter of the manifold plate and prevents any vacuum leaks from the chamber around the joint between the manifold plate and the cast base (13). The hold down retaining bracket (16) applies pressure downward upon the outer periphery of the manifold plate maintaining the seal. The vacuum passage through the vacuum line (18) and the vacuum nipple connection (19) is disclosed in cross section which, when vacuum source is applied, will reduce the pressure in the vacuum chamber and drain off any fluids accumulating in the low point of the chamber.

Figure 3:
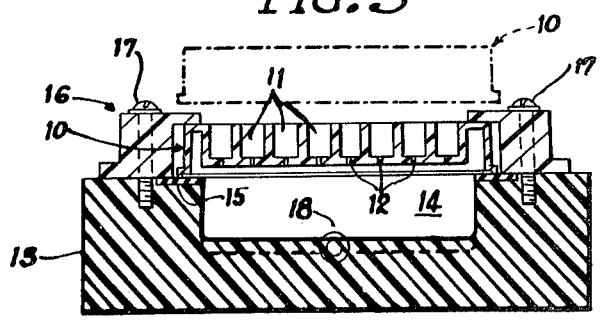
FIG. 3 is a vertical cross section of the device taken across a line running vertically through and bisecting the device of FIG. 1.

A further cross sectional view is provided in FIG. 3 illustrating that the manifold plate (10) is removably positioned over the vacuum chamber (14). The manifold plate is shown in cross section in position and securely held by the protruding lip of the retaining bracket (16), which is in place fastened to the cast base (13) by bolt (17). To remove the manifold plate and the tested samples contained therein, the bolts need only be loosened and the manifold plate removed from the retaining brackets as shown in shadow view of the plate (10).

Figure 4:
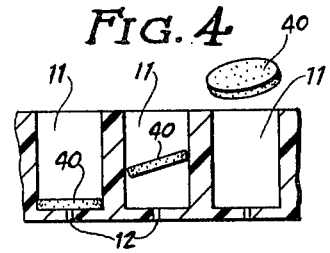
FIG. 4 is a partial vertical cross section across the manifold plate showing insertion of the filter elements.
Figure 5:
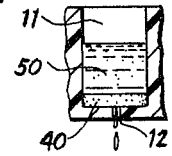
FIG. 5 is a partial cross section of the manifold plate illustrating flow of the test fluid.
Figure 6:
FIG. 6 is a partial cross section of the manifold plate illustrating deposit of the test solid on the filter medium.

FIG. 4 illustrates the method of insertion of the filter medium in the present embodiment as merely dropping in a small disc of filter paper (40). From right to left, the three sample cups of the partial cross section are shown with the filter paper about to be positioned being inserted and finally resting in the bottom of the well positioned over the drain hole (12). In operation, FIGS. 5 and 6 illustrate that a fluid to be tested (50), which can be any biochemical or other solution suspending a solid or separable dissolved constituent, is placed in the sample well over the filter medium (40). Drain hole (12) is of a size that surface tension of the fluids will prevent flow through the hole until a sufficient vacuum is applied on the downstream side of the hole to break the surface tension.

FIG. 6 finally illustrates the filtering process complete and the residues symbolically shown deposited upon the surface of the filter disc. At this point, depending on the test sequence, a variety of operations may be performed. For instance, without removing the filter, the test object may be washed with a cleansing agent which will be drawn again through the filter and drain hole by applying a vacuum, or a reactive agent may be applied and left in the well for the proper process time before vacuum is applied to withdraw it again through the drain hole. The whole process of filtration and washing can be completed in 30 seconds. The entire plate may be removed with the tested substances for test operations apart from the suction base, as for incubation or merely storage while the suction base is used with another manifold plate for other tests. A last option is that the filter disc with its deposited residue may be removed for individual testing or storage following the liquid removal operation.

FIG. 7 illustrates an alternative embodiment of the manifold plate. The longitudinal cross section of FIG. 7 discloses that the manifold plate (70) is composed of two hinged sections rather than the unitary plate of FIG. 1. The object of the alternative embodiment is to enable use of a single sheet of filter paper (74) rather than insertion of small discs of filter paper in each well as in FIG. 4. The filter paper is sandwiched in between the upper section (71) and the lower section (72) which is aligned during closing by the hinge (73). The upper section contains test wells (75) similar to those disclosed in the first embodiment discussed, except that they are completely open at both ends. The bottom unit aligns a similar well (76) having a closed surface at its upper end containing a drain hole (77). In the closed position the filter paper is sandwiched between the upper open well and the bottom closed well and drain hole.

FIG. 8 illustrates in partial cross section the unit in closed position with a top open well (75) aligned over a closed bottom well (76) and drain hole (77) with a section of the sheet of filter paper (74) sandwiched in between. The entire closed unit may then be placed in the cast base over the vacuum chamber in the same manner as discussed above concerning FIG. 3 and a test operation may be performed in identical fashion, filling the wells with a test fluid and applying a vacuum to draw the fluid through the filter paper and drain hole. The end result of a test using the alternative embodiment will be a grid pattern of deposited residue on a single sheet of filter paper, providing convenience of indexing, accuracy of tracking samples through the test process, ease of comparison of various samples tested and efficiency of storage of test samples.

Having thus described my invention, I claim:

1. A laboratory test device for capturing substances suspended in a liquid comprising:
   a. a plate formed to define a plurality of wells to contain the liquid samples to be tested,
   b. a drain in each said well consisting of a hole of a diameter such that surface tension of the liquid will maintain the liquid above the hole,
   c. a filter medium placed within the well to cover the drain hole,
   d. an enclosed vacuum chamber joined to the bottom of said plate,
   e. gasket means sealing the joined surfaces of the plate and vacuum chamber to prevent loss of vacuum pressure,
   f. connecting means from said vacuum chamber to a vacuum source of sufficient size to draw the liquid of the test sample through the filter and drain hole leaving suspended solids of the test sample deposited upon said filter medium.

2. A method of entrapping a substance suspended in a liquid medium for sequential reaction and washing steps comprising:
   a. placing a filter medium in a manifold test container consisting of a plurality of wells, each with an outlet hole at its lower surface, said hole of such size that surface tension of the liquid medium will prevent flow at normal atmospheric pressure,
   b. placing a liquid test sample in each said well,
   c. applying a vacuum to the outlet hole sufficient to break the surface tension of the liquid carrier drawing the liquid through the filter medium and the outlet hole depositing suspended particles on the filter medium,
   d. placing reactive agents in each said well for test operation on each said test sample,
   e. again applying a vacuum to withdraw liquid and deposit particulate matter on the filter,
   f. placing cleansing agents in each said well for washing operation of each sample,
   g. again applying a vacuum to withdraw the liquid and deposit particulate matter on the filter medium,
   h. analyzing the particulate residue on the filter medium following the final vacuum withdrawal of liquid.

3. The method of claim 2 in which the analysis is accomplished by radio-isotope detection.

4. The method of claim 2 in which the analysis is accomplished by spectrophotometry.

5. The method of claim 2 in which the analysis is accomplished by microscopy.

6. The method of claim 2 in which the analysis is accomplished by chemical reaction.

7. Apparatus for use in laboratory testing procedures to capture substance suspended in a liquid, comprising:
   a. a first plate element formed to define a plurality of elongate passages sufficiently open to permit substantially unobstructed fluid flow therethrough,
   b. a second plate element formed to define a plurality of drain apertures adapted to register with said passages, each of said apertures being sized such that surface tension of the liquid will prevent the liquid from flowing through the aperture freely, c. a sheet of filter medium positioned between said first and second plate elements,
d. means sealing said first and second plate elements together with said passages and said drain apertures in registry with one another,
e. means defining a vacuum chamber sealed to the bottom of said second plate,
f. connecting means for connecting said vacuum chamber to a vacuum source, whereby said liquid may be drawn through said filter medium and said drain hole, leaving said substances deposited upon said medium.

8. The apparatus of claim 7 wherein said sealing means includes a hinge element joining said first and second plate elements to permit replacement of said sheet and reuse of said apparatus, while maintaining registry of said passages and said drain apertures.

* * * * *